United States Patent [19]
Braeuning

[11] Patent Number: 5,550,602
[45] Date of Patent: Aug. 27, 1996

[54] APPARATUS AND METHOD FOR EXAMINING VISUAL FUNCTIONS

[75] Inventor: Johannes Braeuning, Schwarzwaldstrasse 11, 73760 Ostfildern, Germany

[73] Assignees: Johannes Braeuning, Ostfildern; Stefan Schueller, Tuebingen, both of Germany

[21] Appl. No.: 338,199

[22] Filed: Nov. 9, 1994

[51] Int. Cl.$^6$ .................................................. A61B 3/02
[52] U.S. Cl. .......................... 351/243; 351/239; 351/246
[58] Field of Search ................................. 351/243, 239, 351/237, 246, 224, 226, 201, 200

[56] References Cited

U.S. PATENT DOCUMENTS

| | | |
|---|---|---|
| 2,795,993 | 6/1957 | Leverett et al. . |
| 3,936,162 | 2/1976 | Krakau et al. ............................ 351/17 |
| 4,634,243 | 1/1987 | Massof et al. . |
| 4,869,589 | 9/1989 | Blair et al. . |
| 5,078,486 | 1/1992 | Evans ...................................... 351/243 |
| 5,331,358 | 7/1994 | Schuerle et al. . |

FOREIGN PATENT DOCUMENTS

| | | |
|---|---|---|
| 2096791 | 10/1982 | European Pat. Off. . |
| 0363610 | 4/1990 | European Pat. Off. . |
| 0456166 | 11/1991 | European Pat. Off. . |
| 3003588 | 8/1981 | Germany . |
| 3246854 | 7/1983 | Germany . |
| 3825789 | 5/1990 | Germany . |
| 2140935 | 12/1994 | United Kingdom ................... 351/222 |

Primary Examiner—William L. Sikes
Assistant Examiner—Hung Xuan Dang
Attorney, Agent, or Firm—Evenson, McKeown, Edwards & Lenahan, P.L.L.C.

[57] ABSTRACT

Examinations of the visual field required a spatially large system in the form of a perimeter or a (noise-field) campimeter with a microcomputer, a control and a video monitor. Additional testing apparatuses were required for further examinations. A compact apparatus is provided which can be transported and handled easily for determining visual field defects and for carrying out further examinations, such as testing distance and near vision, vision in the case of an approaching-light glare, testing strabismus, stereo tests, color tests and tests for measuring a reaction. For this purpose, a computer-controlled measuring apparatus is provided by way of a display and a lens system. The apparatus is housed in a spectacle-type and/or helmet-type carrier while the dimensions are small.

13 Claims, 2 Drawing Sheets

APPARATUS AND METHOD FOR EXAMINING VISUAL FUNCTIONS

BACKGROUND AND SUMMARY OF THE INVENTION

This invention relates to an apparatus for examining at least one visual function in the eye of a test subject, including an optical apparatus portion which contains a relatively small-surface image-generating display screen for offering optical test objects at different angles with respect to the optical axis and a computer control for controlling the display screen. This invention further relates to a method which can be carried out by means of this apparatus. Apparatuses of this type are used for examining visual field defects or changes of the perception threshold per retina site under various marginal conditions, for example, examinations, such as perimetry or noise field campimetry. In addition, the apparatus permits the measuring of the visual acuity for the near and the distant region as a function of the brightness of the environment; the measuring of night vision under realistic conditions including blinding glare which may occur in traffic; color tests under adaptation conditions; and stereometric tests with the use of a binocular representation as well as examining strabismus including the determination of the strabismal deviation.

Methods for measuring the visual field are perimetry, campimetry or noise field campimetry. Perimetry discloses the sensitivity to light of any desirable point of the retina. The conventional device used in this case is an arrangement in the form of a spherical perimeter according to Goldmann etc. The test subject fixes on a fixing point offered in the center of the sphere. During this time, light spots are briefly offered to him at various locations within the sphere. He triggers a signal upon recognition. Computer-controlled perimeters are mostly used nowadays. In this case, the computer controls the projection of the testing spots with a site-dependent light intensity according to the physiological perception threshold of the retina at different sites within the sphere.

The method is also used in the form of campimetry. In this case, only the central field of vision of 30° to 60° eccentricity is tested by way of a video monitor. This type of testing is known, for example, from U.S. Pat. No. 4,634,243. In the case of campimetry, the patient fixes according to the same principle on a video monitor at a defined distance.

Noise field campimetry, as disclosed, for example, in European Patent Application 88112691.6, offers a noise field on the display screen in the manner of a television image "without reception". When viewing this noise field, in the case of existing visual field defects, the test subject can perceive these as a scotoma (brighter dark spot) in the noise field.

From European Patent Application EP 0 363 610A1, the projection of testing spots is known by way of a computer-controlled electromechanically deflectable projector, comprising a light source, a diaphragm and a lens. A certain miniaturization of the perimetric testing method is achieved by the fact that an optical imaging system with an enlarging characteristic is arranged between the light source and the observer point.

For testing the visual acuity, a method is known from U.S. Pat. No. 4,869,589 in which optical test objects are displayed on a computer-controlled monitor. In this case, the test is automated, in which case the patient can report his reaction to the system by way of a keyboard or a mouse.

For testing scotopic vision and sensitivity to glare, portable table top devices with eyepieces are known, for example, from German Patent document DE 30 03 588 C2.

Testing apparatuses in the form of spectacles are known for measuring eye movements, for example, for measuring nystagmus; see, for example, German Patent document 38 25 789 C2 and European Patent document EP 0 456 166 A1.

Current systems for examining visual functions have the problem that their dimensions are very large and the systems are also very expensive as different testing devices require high-expenditure arrangements of an examiner's display screen, a computer control, etc. In the case of the perimeter, the cupola alone has a diameter of between 60 cm and 100 cm. Campimeters are also very large systems as monitors, computer controls and distance devices in the form chin rests and forehead rests are required. Refractometers and other table-mounted units, which are usually based on an optical system of lenses and mirrors, are offered for testing visual acuity. The determination of the strabismal angle takes place by means of correcting prismatic glasses or on a "Harms Wall" (tangent scale according to Harms) measuring 2.5 m * 2.5 m. The majority of the apparatuses are very test-specific and are therefore suitable only for one or a few special tests so that additional equipment must be procured for other tests. Some systems can be operated only in darkened rooms while the brightness of the room cannot be adjusted or is difficult to adjust. Thus, marginal conditions, such as the room brightness, cannot be standardized and can therefore also not be reproduced in a precise manner.

The invention is based on the technical problem of providing an apparatus of the initially mentioned type which measures visual field defects at least in the central 30° to 60° field of vision and has a very compact construction, as well as on a method which can be carried out by means of this apparatus. It is another object to implement such an apparatus and the corresponding method such that, by means of it, subjective tests, such as the determination of the strabismal angle, can be objectified and vision tests can be standardized while the contrast and the room brightness are defined. Furthermore, only one apparatus of this type is to be used for carrying out different testing methods for which a respective separate apparatus had been required up to now.

These objects are achieved by an apparatus for examining at least one visual function in the eye of a test subject, including an optical apparatus portion which contains a relatively small-surface image-generating display screen for offering optical test objects at different angles with respect to the optical axis and a computer control for controlling the display screen. The optical apparatus portion is housed in a spectacletype and/or helmet-type carrier which can be mounted on the test subject and contains an optical imaging system in front of the display screen as well as by a method for examining a test subject by means of fixation, which can be implemented by means of the above-described apparatus. In the method, the position of the eyes by a measuring system and thereby the new position of a stimulus is adapted to the measure deviation from the fixation point. Because of the use of a relatively small-surface display screen in connection with an optical imagining system, a very compact construction is permitted. This allows the whole optical portion of the apparatus to be built in a spectacle-type and/or helmet-type carrier which can be mounted on the test subject, whereby the apparatus can be used in a very mobile and universal manner. As a result of supplementary sensory components, special illuminations as well as a light-proof construction, the functions are combined and standardized in apparatuses which previously were separate.

The method permits an automatic adaptation of the measuring system to changing positions of the eye so that it is not absolutely necessary that the test subject fix his eye always on the same point during a measuring operation of the examination of his visual functions. This also prevents measuring errors which are based on faulty subjective influences.

In this case, the examination of the visual field can be combined with other testing procedures, such as the perception testing after an adaptation to the dark, the measuring of visual acuity for distant vision and near vision, the measuring of the reaction speed of a test subject to an optical stimulus, the determination of strabismal angles, the testing for nyctalopia under traffic conditions with blinding by approaching lights as well as by means of color tests and stereometric tests. Thus, the invention combines different testing apparatuses in the miniaturized form of spectacles or of a helmet and the like. For reducing costs and saving space, it is preferable in this case that the control of the apparatus can be connected to personal computer systems in connection with a plug-in card.

Another advantage of the invention is the fact that the room in which the tests are to be carried out does not have to be darkened, as in the case of conventional methods, but the tests may take place in daylight under standardized brightness conditions.

Another advantage is the optimization of the visual field test in that not only a fixation control is permitted when the stimulus is offered but, in a further development of the invention, faulty fixations can be measured and can automatically be compensated when the stimulus is offered. This not only improves the procedure but also accelerates the test routine because no repetitive measurements have to be carried out.

In the following, the invention will be explained in detail by means of drawings representing a preferred embodiment.

DETAILED DESCRIPTION OF THE DRAWINGS

Figure 1:
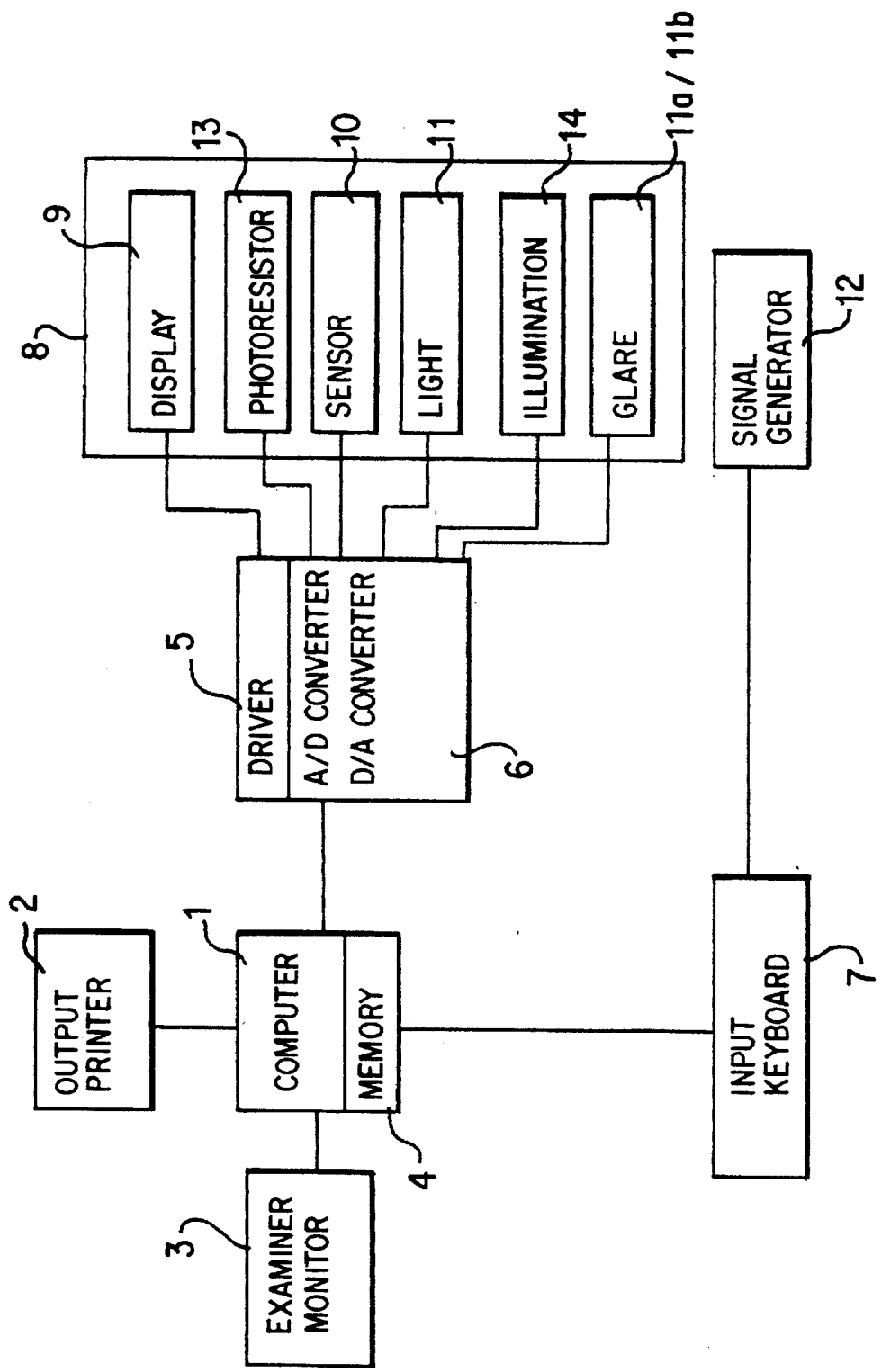
FIG. 1 is a schematic block diagram of an apparatus for examining several visual functions.
Figure 2:
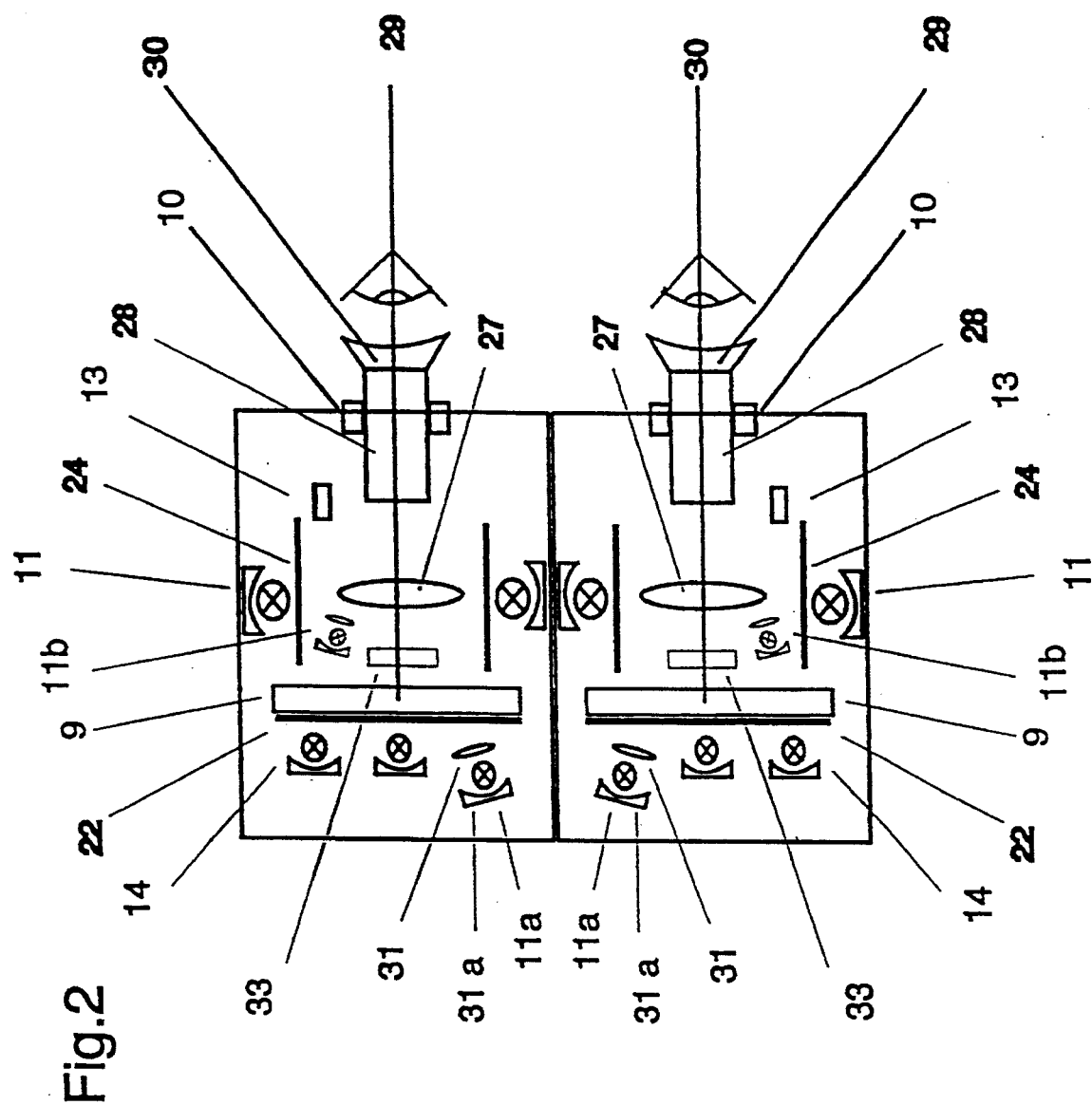
FIG. 2 is a schematic top view of the optical portion of the apparatus of FIG. 1 housed in carrier spectacles.

The apparatus is shown in FIG. 2 as an example in a binocular construction, having halves of the optical apparatus portion which are symmetrical with respect to the center line. If required, the apparatus may also be implemented in a monocular fashion in that only one of the two optical halves is used, in which case the control of the optical portion must be modified in an appropriate manner. Since the optical halves are of identical constructions, the following description explicitly discusses only one half since the function of the other half is obvious. The apparatus is first explained by means of FIG. 1. The optical apparatus portion 8 is constructed in the form of carrier spectacles whose construction is described in more detail by means of FIG. 2 below, and comprises a display 9, a photoresistor 13, a sensor 10 for measuring the eye position, and light sources 14 for regulating the brightness of the display 9, for regulating a glare device 11a/11b as well as for regulating the brightness in the interior of the spectacles 11, 8. In this case, the display 9 can be connected with a computer 1 by way of a driver 5 and the other units 10, 11, 11a, 11b, 13, 14 of the spectacles 8 can be connected with the computer 1 by way of an A/D (D/A) -converter 6. The optical test objects or images are generated in the computer 1 by the software and are shown on the display 9 by way of the driver 5. In this case, the software of the computer controls the shape, the size, the appearance time, the brightness and the color of the optical test objects and the background as well as the localization on the display.

For examining the field of vision, an optical fixation mark is first offered to the test subject which is usually situated in the center of the display 9. The fixation mark is the reference point for the indication of the angle of other test marks represented on the display 9 in the course of the test and is indicated as 0 degrees in its localization. While the test subject fixes his eye on this point, according to the principles of grid perimetry, of static perimetry or of dynamic perimetry, optical test objects (testing marks) are offered which are controlled by the computer 1 with respect to their localization and brightness. When the test subject perceives an optical test object, he actuates a signal generator 12. The signal generator 12 can transmit the signal by way of an analog/digital converter or, as described here, by way of a keyboard 7.

The computer 1 stores the signal with the pertaining localization (angle of view) and the intensity of the tested optical test object in a memory 4. In this case, the fixation control takes place by way of the sensor 10. The optical test objects can also be offered when the fixation is self-willed or faulty because, as the result of the real-time measurement of the eye position by way of the sensor 10, the projection localization of the optical test objects can be corrected. The examiner can follow the current state of the test on an examiner's monitor and can influence the course of the examination. The examiner carries out the overall control of the course of the examination by way of the pertaining software. The input by the examiner takes place by use of the keyboard 7. The examiner is also capable of controlling the brightness in the interior of the spectacles 8 as well as, in the case of passive displays, the illumination brightness and the brightness of the glare device 11a, 11b. A photoresistor 13 measures the brightness in the interior of the spectacles and transmits the signal by way of the analog/digital converter 6 back to the computer 1. Inversely, the brightness of the interior lighting is controlled by the computer 1 by way of the analog/digital or digital/analog converter 6. The output of all measured values continuously takes place on the examiner's monitor 3. The determined data may then be documented in a standardized manner by way of a printer 2 or another output device or may be filed in a memory 4. It is also possible to process the measured data directly in the computer 1 by way of algorithms, fuzzy logic or similar diagnostic aids. Thus, comparative values with respect to earlier examinations may be determined directly or measured values may be directly analyzed and documented.

FIG. 2 is a schematic representation of the measuring spectacles 8. The optical media are entered along the optical axis 29. The test subject looks at the display 9 by way of a corresponding eyepiece 28 as well as a pertaining field lens 27. These elements may be moved electrically or manually in order to correct possible refraction abnormalities of the test subject or in order to present the image or optical test object under conditions of distance vision or close vision. Additional lenses may also be inserted. The correspondingly changed image angle is taken into account in the control.

In the case of a passive display, which this is, the display 9 is illuminated from the rear. This takes place either by way of an illumination 14 by use of a diffuser 22 or by way of an active electroluminescence display. The brightness of the display 9 may be controlled by the examiner in that he controls the brightness of the display illumination 14 or the display 9 itself. The display 9 is capable of displaying discrete shades of gray or gradations of colors. The pixels themselves as well as combinations of pixels (images, optical test objects, etc.) can be controlled. Analogously, it is possible to install an active display with the correspondingly required characteristics.

The approaching-light glare device 11a/11b is constructed of the light source, the reflector 31a and, for focussing the light beam, the pertaining lens 31. In order to permit an approaching-light glare, the glare unit 11a/11b can be inserted either directly in front of the display—see 11b—or behind the display 9 —see 11a. In the second case, the diffuser 22 would be provided with a recess at this point in order to be able to focus a light cone from the illuminating unit 11a behind the display on the eye. As an alternative, the glare light may be reflected in by way of a semitransmitting mirror 33. The brightness in the interior of the spectacles can be controlled by way of additional illuminating units 11 and a pertaining diffusor 24. If required, a color filter may be inserted between this lighting source 11 and the diffusor 24.

A photoresistor 13 measures the brightness in the interior of the spectacles. Furthermore, the sensor 10 measures the position of the eye (or of the eyes) in real time and reports the result by way of the converter 6 to the computer 1. In this case, the sensor 10 may be arranged on or in front of the eyepiece 28 or may also be reflected in by a semitransmitting mirror. It is used for measuring the eye position of the test subject. If required, a camera system for displaying the eye may also be reflected in by way of the semitransmitting mirror 33. The whole unit is closed off to the outside in a light-tight manner. The transition from the test subject to the measuring spectacles is made possible by an elastic collar 30.

In addition to the above-described measuring of the field of vision, the apparatus permits further examinations of the visual functions as described below; in which case, according to the requirements, one or several of the components may be provided in addition to the explicitly indicated components.

A noise field can be displayed on the display 9 in order to make scotomas immediately visible to the test subject.

For testing the visual acuity, optical test objects in different sizes and shapes and having a high contrast are offered to the test subject while the interior brightness is defined. The test subject reports to the examiner what he is seeing. The examiner compares the results with those of his monitor 3. By way of the optical imaging system 27, 28, the virtual distance, under which the test objects appear (virtual test distance), can be varied for testing visual acuity in the near and in the distant region. This variation of virtual test distance can be achieved by the displacement of the optical system or by the exchange of the optical system. By using the possibility of motorized adjustment, by use of two signal generators, which in this case move the lens system, the test subject can indicate the range of virtual test distances which furnishes for him a sharp image (accommodation width).

Furthermore, the visual acuity test may take place under glare conditions (mesoptometry). In this case, the test subject is blinded by a focussed light cone. The glare device 11a may be situated behind the display 9. The media which must then be penetrated are obvious to the person skilled in the art, for example, implemented by a light transmitting opening fitting in size for the diffuser in the diffuser 22 and the display 9. Furthermore, the glare device 11b may be inserted in front of the display 9, or the glare light may be reflected in by way of a semitransmitting mirror 33 which is optionally illustrated in FIG. 2.

For testing the reaction time, optical test objects are offered to the test subject for brief periods of time. The computer 1 measures the time from the offering on the display 9 of the apparatus to the reaction of the test subject by the signal generator 12. In this case, it may be agreed beforehand under which conditions a reaction is to take place, etc.

For examining strabismus or for determining the strabismal angle, the position of the eyes with respect to one another into different viewing directions is tested through the use of a sensor 10 or a so-called eye tracking system. In this case, the viewing directions are indicated by a fixation symbol on the display screen 9. This is possible for distant vision and for near vision. Corresponding to the so-called cover test, the viewing directions and the positions of the eyes can be tested in the case of a brief alternate stimulus sequence.

The apparatus can also have a monocular construction; that is, only one side contains the portion of the apparatus which tests the visual functions, while the other side contains a space whose brightness can be controlled and which, according to the construction, is equipped with individual components. In this case, the apparatus may be used alternately by rotation or exchange of the two sides. The binocular construction has on each side respectively the complete portion of the apparatus which tests the visual functions.

For stereo tests in the case of a binocular construction, images or optical test objects are offered which have different disparity levels. This is possible for distant vision and for near vision. While the disparity decreases, the test subject must then identify, for example, spatially projecting optical test objects, symbols or image contents.

For testing the ability to differentiate between colors, one video screen half per eye is offered to the test subject which has a defined color and brightness. By way of the two signal generators, the test subject can match the other half of the video screen to the defined half. Furthermore, different color gradations may be offered which are to be classified by the test subject. This may take place by way of the two signal generators. Furthermore, images may be offered in the sense of Ishihara plates.

By means of a further development of the invention for testing the dark/light adaptation in a time sequence, the brightness of the space and/or the brightness of the optical test object to be identified can be changed.

All functions of the apparatus are in each case controlled by way of the pertaining software and can be varied with respect to the type of the construction possibilities.

The advantages achieved by the invention are that, as a result of the conception of the apparatus, a small and handy measuring apparatus was created in contrast to the known large systems. The combination of the possible measuring operations permits the concentration of the functions of several systems on a single apparatus which measures the important visual functions (field of vision, visual acuity, night vision, reaction to optical impressions), as required, for example, when driving an automobile. As a result of the construction with low-cost elements and the utilization of existing elements (computer), it is possible to integrate the system into already existing systems. This results in a significant reduction of costs and a saving of space. Because the apparatus can be used without any problems in normal daylight, the operation becomes uncomplicated and convenient. Summarizing, there is the possibility for wide-spread use of the apparatus, for example, also among optometrists. In screening tests, these apparatuses may contribute to the diagnosis of dangerous eye diseases, such as glaucoma. Within this scope, the algorithms of the software already provide information with respect to measured pathological values.

The apparatus may also be used in connection with a video camera as an image enhancing device for visually impaired persons.

Although the invention has been described and illustrated in detail, it is to be clearly understood that the same is by way of illustration and example, and is not to be taken by way of limitation. The spirit and scope of the present invention are to be limited only by the terms of the appended claims.

What is claimed is:

1. Apparatus for examining at least one visual function in an eye of a test subject, comprising:

an optical apparatus portion which contains a relatively small-surface image-generating display screen having controllable pixels for offering optical test objects at different angles with respect to an optical axis;

a computer control for controlling the display screen;

one of a spectacle-type and helmet-type carrier which can be mounted on the test subject and houses the optical apparatus portion; and a focussing optical imaging system contained in the carrier through which the optical test objects offered by the display screen are viewed, said optical imaging system being arranged in front of the display screen.

2. Apparatus according to claim 1, further comprising at least one signal generator which can be operated by the test subject and which is connected with the computer control.

3. Apparatus according to claim 1, wherein the carrier encloses a space between the display screen and an observer point in a light-tight manner.

4. Apparatus according to claim 3, further comprising a controllable illuminating device and a brightness sensor which are connected with the computer control for adjusting a brightness and a color of the light-tight space.

5. Apparatus according to claim 1, further comprising means for measuring eye position and eye movements.

6. Apparatus according to claim 1, wherein the computer control comprises a computer for measuring, analyzing and controlling at least one of perimetry, noise field campimetry, mesoptometry, distant vision, near vision, accommodation width, stereo test, strabismal angle determination, dark adaption, reaction capacity and color recognition examinations.

7. Apparatus according to claim 1, wherein further for focussing a display screen image on different virtual distances in front of the observer point, the optical imaging system is adjustable or exchangeable manually or by a motor, and a lens system for the virtual optical image is adjusted to different distances for examining distant vision or near accommodation or can be exchanged.

8. Apparatus according to claim 1, wherein the display screen is one of an active and passive display having one of discrete color, gray gradations, and brightnesses as well as a high resolution and frequency in which case each pixel can be individually controlled.

9. Apparatus according to claim 8, wherein the display is either a passive display, for the illumination of which a lighting device comprising a diffuser is provided, or an electroluminescence display with discrete color gradations, the brightness and the color being controllable by a computer and a front-connected color filter.

10. Apparatus according to claim 1, further comprising a monocular construction for said apparatus, and including a space which is enclosed in a light-tight manner and whose brightness can be adjusted by a lighting device, said apparatus being provided for the eye which is not examined in each case, the function units being exchangeable between the right and the left eye.

11. Apparatus according to claim 1, further comprising by a glare device comprising a light beam which is focussed by an optical system and which can be aligned in each case at a defined angle with one or both eyes, the glare device being capable of being inserted behind the display or in front of the display 9 or of being reflected in.

12. Apparatus according to claim 1, wherein further by way of a semitransmitting mirror at least one of glare light, a measuring system, and an imaging camera system for measuring the eye position can be reflected in.

13. A method for use with an apparatus for examining at least one visual function in an eye of a test subject, the apparatus including an optical apparatus portion which contains a relatively small-surface image-generating display screen having controllable pixels for offering optical test objects at different angles with respect to an optical axis; a computer control for controlling the display screen; one of a spectacle-type and helmet-type carrier which can be mounted on the test subject and houses the optical apparatus portion; a focussing optical imaging system contained in the carrier through which the optical test objects offered by the display screen are viewed, said optical imaging system being arranged in front of the display screen, a method comprising the steps of:

continuously measuring the position of the eyes by a measuring system to determine a fixation point; and adapting a new position of a stimulus on the display screen to a measured deviation from the fixation point.

* * * * *